(12) United States Patent
Patel et al.

(10) Patent No.: US 6,800,477 B2
(45) Date of Patent: Oct. 5, 2004

(54) STEREOSELECTIVE REDUCTION OF SUBSTITUTED ACETOPHENONE

(75) Inventors: Ramesh Patel, Bridgewater, NJ (US); Animesh Goswami, Plainsboro, NJ (US); Linda N. Chu, East Brunswick, NJ (US); Venkata B. Nanduri, East Brunswick, NJ (US); Steven L. Goldberg, Basking Ridge, NJ (US); Robert M. Johnston, Whitehouse Station, NJ (US); Mary Jo Donovan, North Brunswick, NJ (US); K. David Mirfakhrae, North Brunswick, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 121 days.

(21) Appl. No.: 10/092,263

(22) Filed: Mar. 6, 2002

(65) Prior Publication Data

US 2003/0068811 A1 Apr. 10, 2003

Related U.S. Application Data

(60) Provisional application No. 60/278,025, filed on Mar. 22, 2001.

(51) Int. Cl.$^7$ ................................................ C12P 41/00
(52) U.S. Cl. ...................... 435/280; 435/156; 435/911; 435/938
(58) Field of Search ................................ 435/189, 280, 435/255.1, 156, 255.5, 911, 938

(56) References Cited

U.S. PATENT DOCUMENTS 5,391,495 A    2/1995 Patel et al.
5,393,663 A    2/1995 Patel et al.
5,523,223 A    6/1996 Kula et al.

FOREIGN PATENT DOCUMENTS

WO     WO 99/23242 A1    5/1999

OTHER PUBLICATIONS

Bing–nan Zhou et al. J. Am. Chem. Soc., vol. 105, pp. 5925–5926, 1983.
Kazutoshi Ushio et al. Tetrahedron Letters, vol. 27, No. 23, pp. 2657–2660, 1986.
Markus Christen et al. J. Chem. Soc., Chem. Commun. pp. 264–266, 1988.
Antonio Trincone et al., Biotechnology and Bioengineering, vol. 35, pp. 559–564, 1990.
Ramesh Patel et al., Enzyme Microb. Technol., vol. 13, pp. 906–912, 1991.
Ramesh Patel et al., Enzyme Microb. Technol., vol. 15, pp. 1014–1021, 1993.
Ramesh Patel et al., Enzyme Microb. Technol., vol. 14, pp. 731–738, 1992.
Kometani et al., Journal of Fermentation and Bioengineering, vol. 80, No. 2, pp. 208–210, 1995.

*Primary Examiner*—William H. Beisner
(74) *Attorney, Agent, or Firm*—Deanna L. Baxam

(57) ABSTRACT

The present invention is directed to novel stereoselective processes for the preparation of (S)-1-arylethanols by the reduction of the corresponding keto group containing compounds by microorganisms. (S)-1-arylethanols are useful as intermediates in the synthesis of compounds that are inhibitors of γ-secretase useful in the treatment of Alzheimer's disease.

9 Claims, No Drawings

STEREOSELECTIVE REDUCTION OF SUBSTITUTED ACETOPHENONE

CROSS REFERENCE TO RELATED APPLICATION

This non-provisional application claims priority from provisional application U.S. Ser. No. 60/278,025 filed Mar. 22, 2001.

FIELD OF THE INVENTION

The present invention is directed to a novel stereoselective process for the preparation of (S)-1-arylethanol by the reduction of the corresponding keto group containing compounds by microorganisms. The present invention relates to novel processes for the preparation of chiral alcohols by microbial reduction of the corresponding ketones.

BACKGROUND OF THE INVENTION

Bing-nan Zhou et al. *J. Am Chem. Soc.*,Vol. 105, pages 5926–5928, 1983 describe the chemomicrobiological synthesis of L-carnitine, which plays an important role in the human metabolism and transport of long-chain fatty acids. Particularly, this paper teaches the reduction by baker's yeast, i.e. *Saccharomyces cerevisiae*, of ethyl 4-chloroacetoacetate to ethyl (S)-4-chloro-3-hydroxybutanoate.

Kazutoshi Ushio et al *Tetrahedron Letters*, Vol. 27, No. 23, pages 2657–2660, 1986, disclose the reduction of beta-keto esters by methanol grown yeast. This paper teaches that the subject reaction causes dramatic shifts of the enantiomer excess of the resultant product in the direction of the D-isomer. This phenomena was produced when the reaction was carried out utilizing yeast grown in methanol due to enzymes characteristic of yeast grown in such media.

Markus Christen et al. *J. Chem. Soc., Chem. Commun.* pages 264–266, 1988, discloses the synthesis of four stereoisomers of methyl-6-(p-chlorophenylthio)-3,4-dihydrohexanoate in w appropriate yeast reduction. It is stated therein that, although the reduction of beta-keto esters with yeast has been studied extensively, it remains difficult to predict either the absolute configuration of the product(s) or, in particular, the enantiomeric excess likely to be achieved.

Antonio Trincone et al., *Biotechnology and Bioengineering*, Vol. 35, pages 559–564, 1990 describe asymmetric reduction of ketones with resting cells of *Sulfolobus solfataricus*. It is stated that the reductive ability of the resting cells of this organism strongly depends on the phase of cell growth.

Ramesh Patel et al., *Enzyme Microb. Technol.*, Vol. 13, pages 906–912, 1991 describe the stereospecific microbial reduction of 4,5-dihydro-4-(4-methoxyphenyl)-6-(trifluoromethyl-1H-1)-benzazepin-2-one. In particular, it is disclosed that a key intermediate (3R-cis)-1,3,4,5-tetrahydro-3-hydroxy-4-(4-methoxyphenyl)-6-(trifluoromethyl)-2H-1-benzazepine-2-one was made by the stereoselective microbial reduction of the parent ketone. It is stated that it was possible by the selection of specific conditions to obtain a single isomer from among four known possibilities.

Ramesh Patel et al., *Enzyme Microb. Technol.*, Vol. 15, pages 1014–1021, 1993, describes the stereoselective reduction of a diketo compound, 3,5-dioxo-6-(benzyloxy) hexanoic acid, methyl ester, to a single enantiomer of the resulting dihydroxy compound.

Ramesh Patel et al., *Enzyme Microb. Technol.*, Vol. 14, pages 731–738, 1992, describe a process of heat treating *Geotrichum candidum* to improve the optical purity of the hydroxy product obtained from the reduction of beta-keto esters thereby.

Kometani et al., *Journal of Fermentation and Bioengineering*, Vol. 80, No. 2, pages 208–210, 1995, teaches yeast-mediated bioreduction utilizing ethanol as the energy source. The relationship between the rate of consumption of ethanol and the prochiral ketone reduction rate in Baker's Yeast is examined and it is concluded that ethanol could be applicable to large-scale production of chiral alcohols from prochiral ketones.

Ramesh Patel et al., U.S. Pat. No. 5,391,495, issued Feb. 21, 1995, discloses the stereoselective reduction of certain keto-containing sulfonamide compounds to form the corresponding hydroxyl group-containing compounds utilizing a microorganism or an enzyme capable of catalyzing the reduction. The enzymes named are oxido-reductase or dehydrogenase and the microorganisms are preferably selected from Hansenula, Rhodococcus and Norcardia species.

SUMMARY OF THE INVENTION

The present invention is directed to a novel stereoselective process for the preparation of (S)-1-arylethanol by the reduction of the corresponding keto group containing compounds by microorganisms. The present invention relates to novel processes for the preparation of chiral alcohols by microbial reduction of the corresponding ketones in order to synthesize, inter alia 4-[2-((1R)-1-{[(4-chlorophenyl)sulfonyl]-2,5-difluoroanilino}ethyl-5-fluorophenyl]butanoic acid which is a novel γ-secretase inhibitor for the treatment of Alzheimer's disease.

Thus according to a first aspect of the present invention is provided a process for the preparation of compounds of Formula (I)

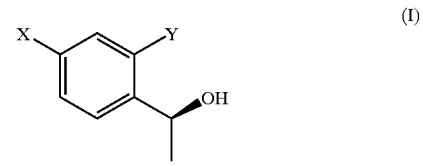

wherein
X and Y are each independently selected from the group consisting of H, Cl, Br, I and $R^1$;
$R^1$ is substituted or unsubstituted alkyl, alkenyl or $(CH_2)_nCOR^2$;
n is an integer from 1 to 10;
$R^2$ is OH, $OR^3$ or $NH_2$; and
$R^3$ is substituted or unsubstituted alkyl, alkenyl, $C_{3-7}$ cycloalkyl or substituted or unsubstituted aryl;
by stereoselective reduction of a compound of Formula (II)

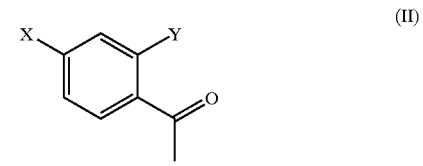

wherein
X and Y are each independently selected from the group consisting of H, Cl, Br, I and $R^1$;

$R^1$ is substituted or unsubstituted alkyl, alkenyl, or $(CH_2)_nCOR^2$;

n is an integer from 1 to 10;

$R^2$ is OH, $OR^3$ or $NH_2$; and $R^3$ is substituted or unsubstituted alkyl, alkenyl, $C_{3-7}$ cycloalkyl or substituted or unsubstituted aryl;

by reaction with an oxidoreductase enzyme capable of catalyzing the enzymatic reduction of ketones represented by Formula (II).

According to a second aspect of the present invention is provided a process for the preparation of compounds of Formula (I)

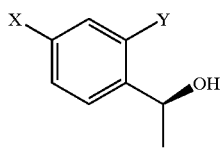

(I)

wherein

X and Y are each independently selected from the group consisting of H, Cl, Br, I and $R^1$;

$R^1$ is substituted or unsubstituted alkyl, alkenyl, or $(CH_2)_nCOR^2$;

n is an integer from 1 to 10;

$R^2$ is OH, $OR^3$ or $NH_2$; and $R^3$ is substituted or unsubstituted alkyl, alkenyl, $C_{3-7}$ cycloalkyl or substituted or unsubstituted aryl;

by stereoselective reduction of a compound of Formula (II)

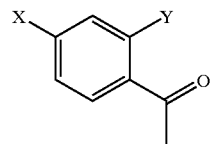

(II)

wherein

X and Y are each independently selected from the group consisting of H, Cl, Br, I and $R^1$;

$R^1$ is substituted or unsubstituted alkyl, alkenyl, or $(CH_2)_nCOR^2$;

n is an integer from 1 to 10;

$R^2$ is OH, $OR^3$ or $NH_2$; and $R^3$ is substituted or unsubstituted alkyl, alkenyl, $C_{3-7}$ cycloalkyl or substituted or unsubstituted aryl;

by reaction with a microorganism that supplies an oxidoreductase enzyme capable of catalzying the enzymatic reduction of ketones represented by Formula (II).

Other aspects and embodiments of the present invention are provided for hereinbelow.

DETAILED DESCRIPTION OF THE INVENTION

The stereoselective reduction of the compound represented by formula II above to form the compound represented by formula I is carried out in accordance with the present invention by reaction with an oxidoreductase enzyme, or preferably, a microorganism that supplies an oxidoreductase enzyme capable of catalyzing the enzymatic reduction of the ketones represented by formula II. The cells of the microorganism may be in the form of intact wet cells or dried cells such as lyophilized, spray-dried or heat-dried cells, or in the form of treated cell material such as ruptured cell or cell extracts. While a large and varied number of microorganisms are known to supply some form of oxidoreductase, it has been found in accordance with the present invention that only selected species of Rhodococcus, Brevibacterium, Saccharomyces, Candida, Geotrichum, Rhodotorula, Pichia, Hansenula, Nocardia, Mucor Sphingomonas, Baker's yeast catalyze the reduction of the compound represented by formula II to form the desired compound of formula I in high quantitative and enantiomeric yield. These species are *Rhodococcus erythropolis* ATCC 4277, *Rhodococcus erythropolis* DSM 6971 and *Rhodococcus sp.* ATCC 21227, *Rhodococcus erythropolis* ATCC 27854 *Candida sonorensis* ATCC 56511, *Candida boidinii* ATCC 26175 and ATCC 56507, *Candida guilliermondii* ATCC 9058, *Candida utilis* ATCC 9950, *Candida parapsilosis* ATCC 52820, *Geotrichum candidum* 34614 and ATCC 34014, *Rhodotorula glutinis* ATCC 26207 and ATCC 201718, *Hansenula fabianii* ATCC 58045, *Hansenula polymorpha* ATCC 58401 ATCC 34438 and ATCC 26012, *Hansenula saturnus* ATCC 16762, *Nocardia salmonicolor* ATCC 19149, *Pichia anomala* ATCC 66094, *Pichia capsulata* ATCC 29204, *Pichia methanolica* ATCC 56510, ATCC 56508 and ATCC 58403, *Pichia pinus* ATCC 28780, *Pichia silvicola* ATCC 16764, *Pichia stipitis* ATCC 59785, *Sphingomonas paucimobilis* ATCC 202027, *Saccharomyces cerevisiae* ATCC 12341 and ATCC 44953, *Nocardiodes albus* ATCC 55425, *Mucor rouxii* ATCC 24905, *Mucor hiemalis* ATCC 16636 and *Brevibacterium sp.* ATCC19653. The term "ATCC" as used herein refers to the accession number of the depository for the particular organism, i.e. the American Type Culture Collection, 12301 Parklawn Drive, Rockville, Md. 20852. The term "DSM" refers to the German Collection of Microorganisms and Cell Cultures, Branschweig, Germany. The use of genetically engineered organisms is also contemplated. The host cell may be any cell, e.g., *Eschericia coli*, modified to contain a gene or genes for expressing one or more enzymes capable of catalysis as described herein.

As utilized herein, the following terms have the definitions given below. The term "alkyl" refers to optionally substituted straight-or branched-chain saturated hydrocarbon groups having from 1 to 10 carbon atoms, preferably from 1 to 4 carbon atoms.

The term "alkenyl" refers to optionally substituted straight-or branched-chain unsaturated hydrocarbon groups having from 1 to 10 carbon atoms, preferably from 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryl, aryloxy, aralkyl, alkanoyloxy, amino, alkylamino, arylamino, aralkylamino, cycloalkylamino, heterocycloamino and disubstituted amino.

The term "substituted alkenyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryl, aryloxy, aralkyl, alkanoyloxy, amino, alkylamino, arylamino, aralkylamino, cycloalkylamino, heterocycloamino and disubstituted amino.

The term "aryl" refers to monocyclic or bicyclic aromatic hydrocarbon groups having from 6 to 12 carbon atoms in the ring portion, for example, phenyl, naphthyl, biphenyl and diphenyl groups, each of which may be substituted.

The term "substituted aryl" refers to an aryl group substituted by, for example, one to four substituents such as alkyl; substituted alkyl, halo, trifluoromethyl, trifluoromethoxy, hydroxy, alkoxy, cycloalkyloxy, heterocyclooxy, alkanoyl, alkanoyloxy, amino, alkylamino, dialkylamino, aralkylamino, cycloalkylamino, heterocycloamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkylsulfonyl, sulfonamido, aryloxy and the like. The substituent may be further substituted by one or more members selected from the group consisting of halo, hydroxy, alkyl, alkoxy, aryl, substituted alkyl, substituted aryl and aralkyl.

With respect to the use of microorganisms, the enzymatic reduction method of the present invention may be carried out subsequent to the fermentation of the microorganism employed, i.e. as a two-stage fermentation and reduction, or concurrently therewith, i.e. as a single-stage or in situ fermentation and reduction. In the latter, the microorganism may be grown in an appropriate medium, especially one containing nitrogen and carbon sources, until sufficient growth is realized and then a compound selected from those compounds represented by formula II is added thereto. The enzymatic reduction is thereafter continued until virtually complete conversion of the compound represented by formula II is attained.

In the two-stage methodology, the microorganism is initially grown in a suitable medium as described above until it exhibits a predetermined level of enzymatic activity at which point the cells are harvested by conventional separation techniques and microbial cell suspensions prepared therefrom containing appropriate buffering agents and the like. Suitable buffering agents include phosphate buffers, particularly sodium or potassium phosphate buffer, tris-HCl, sodium acetate and the like. Water may also be used to prepare suspensions of microbial cells. The compound represented by formula II is then added thereto and the enzymatic reduction continued until the conversion is virtually complete. In either instance, the appropriate growth medium will include, as previously stated, sources of carbon and nitrogen and trace elements. Inducers may be added as well. As those of ordinary skill in the art are aware, the term inducer means any compound initiating or enhancing the desired enzymatic, i.e. oxidoreductase, activity within the cell to produce the desired product. The compound represented by formula II would be considered an inducer, particularly when added in small quantities during the growth of the microorganism.

Suitable carbon sources for the medium may include sugars, such as maltose, lactose, glucose, fructose, glycerol, sorbitol, sucrose, starch, mannitol, propylene glycol and the like, organic acids and their salts such as sodium acetate, sodium citrate and the like, amino acids and their salts, such as sodium glutamate and the like, and alcohols, such as ethanol, propanol and the like. Suitable nitrogen sources may include N—Z amine A, corn steep liquor, soy bean meal, beef extracts, yeast extracts, molasses, baker's yeast, tryptone, nutrisoy, peptone, yeastamin, sodium nitrate, ammonium sulfate and the like. Suitable trace elements may include phosphates, and magnesium, manganese, calcium, cobalt, nickel, iron, sodium and potassium salts. The appropriate media utilized in accordance with the present invention may include a plurality of constituents selected from any of these categories. Representative preferred media include without intended limitation aqueous media containing the following, in weight percent:

| | Ingredient | Weight Percent |
|---|---|---|
| No. 1 | Malt Extract | 1% |
| pH 7.0 | Yeast Extract | 1% |
| | Peptone | 1% |
| | Glucose | 2% |
| No. 2 | Malt Extract | 1% |
| pH 7.0 | Yeast Extract | 1% |
| | Peptone | 0.3% |
| | Glucose | 4% |
| No. 3 | Malt Extract | 1% |
| pH 7.0 | Yeast Extract | 1% |
| | Peptone | 0.3% |
| | Glycerol | 2% |
| No. 4 | Malt Extract | 1% |
| pH 7.0 | Yeast Extract | 1% |
| | Peptone | 0.3% |
| | Sodium Succinate | 2% |
| No. 5 | Nzamine A | 1.0% |
| | Yeastamin | 2.0% |
| | Glycerol | 2.0% |
| | $Na_2HPO4$ | 0.6% |
| | $KH_2PO4$ | 0.3% |
| | $(NH4)_2SO4$ | 0.125% |
| | $MgSO4*7H_2O$ | 0.0246% |

After autoclaving the medium No 5, add the filtered sterilized solutions of neomycin (in water) and chloramphenicol (in 200 proof ethanol) to final concentration of 10 mg/L and 33 mg/L, respectively.

Before sterilization, the pH is preferably adjusted to from about 6 to 8, most preferably about pH 6.8. The media are then sterilized, for example, by heating at a temperature of about 121° C. for 30 minutes. Following sterilization, the media are adjusted to pH 6.5 to 7.5, most preferably about pH 7.0. During microbial growth and the reduction process, the pH is maintained at between about 4.0 and 9.0, preferably between about pH 6.0 and 8.0. An appropriate base or acidic salt from among the constituents named above can conveniently be utilized for adjustment of the pH.

The temperature of the reaction mixture is a measure of the heat energy available for the reduction process, and for this reason, a suitable temperature should be maintained to ensure that there is sufficient energy available for the process to go to completion. A suitable temperature range for the process of the invention is in the range of from about 5° C. to about 60° C., preferably from about 25° C. to about 40° C. Pressure is not known to be critical for the practice of the process of the invention and for convenience about atmospheric pressure is typically maintained.

The process of the present invention is preferably carried out under aerobic conditions. Agitation and aeration of the reaction mixture is also beneficial to the subject process in that it affects the amount of oxygen available for the biotransformation. The process is advantageously carried out, for example, in shake-flask cultures or fermentor tanks during the growth of the microorganisms in a single-stage or two-stage process as described above. Agitation in the range of from about 10 to 1000 RPM is preferred, with from about 50 to 500 R.P.M. being most preferred. Aeration of from about 0.1 to 10 volumes of air per volume of media per minute (v/Vt.) is preferred, with aeration of about 5 volumes per volume of media per minute being particularly preferred.

Complete conversion of the compound represented by formula II may require, for example, from about 1 to 72 hours, typically from about 4 to 48 hours, measured from the time of addition of the compound represented by formula II to the media. It is preferred that the media be aqueous based, although an organic liquid or a miscible or immiscible, i.e. biphasic, organic/aqueous liquid mixture may be utilized as well.

The stereoselective enzymatic reduction process of the present invention may be carried out by adding a co-factor such as reduced nicotinamide adenine dinucleotide (NADH) or nicotinamide adenine dinucleotide phosphate (NADPH), especially when an isolated enzyme would be utilized. NADH or NADPH, for example, may thereafter be regenerated and reused. A further enzyme that regenerates the NADH or NADPH in situ may be employed such as formate dehydrogenase, glucose-6-phosphate dehydrogenase or glucose dehydrogenase. Suitable hydrogen donors include molecular hydrogen, a formate (e.g. an alkali metal or ammonium formate), glucose, a hypophosphite or an electrochemical reduction in the presence of a viologen, for example methyl viologen. It is also possible to regenerate NADH or NADPH without further enzymes using, for example, ethanol or formate.

It is further preferred to add the compound of formula II to the reaction media so that it is from about 0.2% to about 5% by weight, based on the combined weight of starting compound and media. The inoculum of microorganism relative to the amount of starting material is sufficient to provide for the enzymatic reduction of the compound represented by formula II with the times described above, generally from about 5 wt. % to about 30 wt. % cells concentration. Utilizing the preferred reaction parameters described above with the microorganisms given will provide a reaction yield of greater than 70%, optimally in excess of 90% and, an enantiomeric excess of greater than 93%, optimally in excess of 99% of the desired enantiomer of the compound represented by formula I. The product of the reduction process of the present invention, i.e. the compounds represented by formula I may be recovered by any suitable methods for isolation and/or purification methodologies such as extraction, resin adsorption/desorption, distillation, crystallization, column chromatography and the like.

It is understood that various other embodiments and modifications in the practice of the invention will be apparent to, and can be readily made by, those of ordinary skill in the art without departing from the scope and spirit of the invention as described above. Accordingly, it is not intended that the scope of the claims appended hereto be limited to the exact description set forth above, but rather that the claims be construed as encompassing all of the features of patentable novelty that reside in the present invention, including all the features and embodiments that would be treated as equivalents thereof by those skilled in the relevant art. The invention is further described with reference to the following experimental work.

EXAMPLE 1

Stereoselective Enzymatic Reduction 2-Bromo-4-fluoro acetophenone (III): Use of Whole Cells—Two Stage Process Various microbial cultures (1 mL) were inoculated into 100 mL of medium 1 as noted above in a 500 mL flask and incubated at 28° C. and 200 RPM on a shaker for 48 hours. Cells were harvested by centrifugation and cells were suspended in 10 mL of 100 mM potassium phosphate buffer, pH 7.0. Glucose was added to the cell suspensions at 25 mg/mL and 15 mg 2-bromo-4-fluoro acetophenone (the substrate, see formula III) was added thereto.

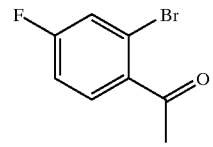

(III)

The biotransformations (reductions) were carried out at 28° C. and 200 R.P.M. on a shaker for 24–48 hours. At predetermined times the reaction mixtures were quenched with four volumes of acetonitrile, mix on the vortex mixer, filtered through a 0.2 micron filter and collected and 1 mL sample was analyzed by HPLC method 1 to determine the substrate and product concentrations. Remaining solution was evaporated to dryness under a stream of nitrogen and the residue taken up with 1 mL of ethanol, filtered and analyzed by HPLC method 2 to determine the enantiomeric excess of product. The results are summarized in Table 1 below. The product for this example is as shown in the formula IV.

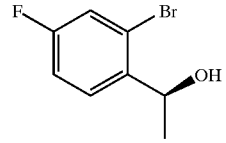

(IV)

Method 1

This method was developed to monitor the reduction of the ketone represented by Formula (III) to the alcohol represented by Formula (IV).
Column: Phenylhexyl (0.46×15 cm, 5μ) From Phenomenex
Mobile Phase: Acetonitrile: Water (1:1)
Flow Rate: 1 ml/min
Column Temperature: 50° C.
Detector: UV at 210 nm
Injection Volume: 5 μl
2-bromo-4-fluoro acetophenone (III) elutes at about 6.3 minutes, S-1-(2'bromo-4'-fluoro phenyl)-ethanol (IV) or its enantiomer elutes at about 5.4 minutes.

Method 2

This method was developed to monitor the enantiomeric purity of the alcohol represented by Formula (IV).
Column: Chiralpak AD (0.46×25 cm, 10 μm, Daicel Chemical Industries Ltd.)
Mobile Phase: 0.249% V/V absolute ethanol in hexane.
Flow Rate: 1 ml/min
Column Temperature: Ambient
Detector: UV at 210 nm.
Injection volume: 2 and 5 μl.
The enantiomers of ((R/S)-1-(2-bromo-4-fluoro phenyl)-ethanol) elute at about 48 (R) and 54 (S) minutes. The substrate, 2-bromo-4-flouro acetophenone, elutes at about 15 minutes.

TABLE 1

Microbial Reduction of 2-bromo-4-fluoro acetophenone to the desired corresponding chiral alcohol

| Microorganism | ATCC | Alcohol % | EE S-Alcohol % |
|---|---|---|---|
| Control | | 0% | |
| Candida sonorensis | 56511 | 100% | 99.2 |
| Candida boidini | 26175 | 100% | 97.4 |
| Candida guilliermondii | 9058 | 100% | 99.0 |
| Candida utilis | 9950 | 99% | 99.6 |
| Candida maltosa | 20184 | 81% | 98.6 |
| Candida kefir | 14244 | 86% | 96.8 |
| Candida parapsilosis | 52820 | 98% | 97.6 |
| Geotrichum candidum | 34614 | 98% | 97.9 |
| Geotrichum candidum | 34014 | 100% | 99.4 |
| Rhodotorula glutinis | 26207 | 100% | 99.0 |
| Rhodotorula glutinis | 201718 | 100% | 99.9 |
| Hansenula fabianii | 58045 | 94% | 99.0 |
| Hansenula polymorpha | 34438 | 100% | 99.8 |
| Hansenula polymorpha | 58401 | 100% | 99.0 |
| Hansenula polymorpha | 26012 | 100% | 99.0 |
| Hansenula saturnus | 16762 | 100% | 99.0 |
| Nocardia salmonicolor | 19149 | 100% | 99.3 |
| Pichia anomala | 66094 | 100% | 99.0 |
| Pichia capsulata | 29204 | 100% | 99.0 |
| Pichia membranafaciens | 20101 | 95% | 99.0 |
| Pichia methanolica | 56510 | 100% | 99.0 |
| Pichia pinus | 28780 | 100% | 99.0 |
| Pichia silvicola | 16764 | 99% | 99.0 |
| Pichia stipitis | 59785 | 100% | 99.0 |
| Sphingomonas paucimobilis | 202027 | 100% | 99.0 |
| Saccharomyces cerevisiae | 12341 | 93% | 99.9 |
| Saccharomyces cerevisiae | 44953 | 72% | 99.3 |
| Active Dry Yeast, Red Star | | 78% | 99.9 |

EXAMPLE 2

Use of Baker's Yeast

The substrate (formula III) and product (formula IV) for this example are as shown in the example 1.

Process Details

Equip a 3 L bioreactor (Braun Biostat B) with a pH electrode. Set impeller speed at 500 R.P.M. and temperature setting at 28° C. Add 800 ml of the 10 mM phosphate buffer (pH 7.0) to the bioreactor. Stir the contents of the bioreactor at 300–500 RPM and maintain the temperature at 28° C. throughout the experiment. Turn on the pump to control the automatic addition of a 10% sodium hydroxide solution to keep the pH constant at 6.0. Add 150 g active dry yeast (from Red Star) slowly over 30 minutes. Add 5 g of 2-bromo-4-fluoro acetophenone. Use a minimum volume of deionized water (5 ml) to wash any residual ketone to the reactor. Add 0.5 ml of SAG antifoam agent if necessary to control the foam. In order to control the foam, an additional 0.5 ml of SAG antifoam can be added now or later as necessary. Start addition of a 25% glucose solution at the rate of 8–10 ml per hour. The entire glucose solution (200 ml) is added over 20–24 hours. Take out 1 ml samples at 4, 8, 12, 20, 22, 24 hours, and more at 2 hour interval if necessary. Analyze as discussed in example 1 for determination of substrate and product concentrations and enantiomeric excess of product. The reaction time of 20–28 hours is usually sufficient for the completion of the reaction. In this process a reaction yield of product was 90% and enantiomeric excess of desired isomer was 99.5%.

EXAMPLE 3

Reduction of Keto Methyl Ester Represented by Formula (V) to the Corresponding Alcohol Represented by Formula (VI)

Various microbial cultures (1 mL) were inoculated into 100 mL of medium 1 or medium 3 as noted above in a 500 mL flask and incubated at 28° C. and 200 RPM on a shaker for 48 hours. Cells were harvested by centrifugation and cells were suspended in 10 mL of 100 mM potassium phosphate buffer , pH 7.0. Glucose was added to the cell suspensions at 25 mg/mL and 10 mg keto methyl ester (the substrate represented by formula V) was added thereto.

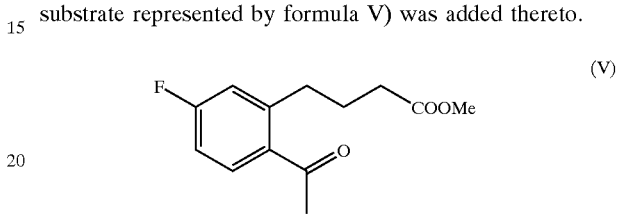

(V)

The biotransformations (reductions) were carried out at 28° C. and 200 RPM on a shaker for 24–48 hours. The reaction mixture was extracted with two volumes of ethyl acetate and evaporated to dryness under a stream of nitrogen. A portion of the ethyl acetate extract was dissolved in acetonitrile and analyzed by HPLC method 3 to determine the substrate and product concentrations. Another portion was dissolved in mixture of hexane:isopropanol (1:1) and analyzed by HPLC method 4 to determine the enantiomeric excess of the product.

The results are summarized in Table 2 below. The product for this example is as shown in the formula VI.

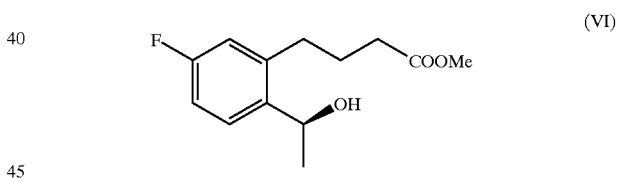

(VI)

Method 3

Column: Kromasil C-8 (0.46×15 cm, 5 micron, Waters)
Mobile Phase: Gradient elution from 100% solvent A (0.2% $H_3PO_4$) and 0% solvent
B (acetonitrile: 0.2% $H_3PO_4$ 90:10) to 70% solvent B at 20 minutes then to 100% solvent B at 25 minutes and continue at 100% solvent B to 30 minutes.
Flow Rate: 1 ml/min, Detection: UV at 210 nm
Retention Times: Keto methyl ester (V) 20.3 minutes and hydroxy methyl ester (VI) 18 minutes.

Method 4

Column: Chiralpak AD (0.46×25 cm, 10 micron, Daicel)
Mobile Phase: Hexane:ethanol:isopropanol (98.32:1.43:0.25)
Flow Rate: 1 ml/min, Detection: UV at 210 nm
The enantiomers of (R/S) hydroxy methyl ester elute at about 23.6 (R) and 31.1 (S) minutes.

TABLE 2

Microbial Reduction of Keto Methyl Ester (Formula (V)) to the corresponding (S)-hydroxy methyl ester (Formula (VI)):

| Name | ATCC # | Hydroxy Ester (Yield) | EE of S-Hydroxy methyl Ester |
| --- | --- | --- | --- |
| Pichia methanolica | 58403 | 40% | >99% |
| Pichia methanolica | 56510 | 41% | 99% |
| Pichia methanolica | 56508 | 33% | >96% |
| Geotrichum candidum | 34614 | 6% | >99% |
| Mortierella ramanniana | 34194 | 5% | ND |
| Apiotrichum humicola | 26699 | 3% | ND |
| Candida boidinii | 56507 | 11% | >99% |
| Nocardiodes albus | 55425 | 4% | ND |
| Nocardiodes luteus | 55426 | 1% | ND |
| Streptomyces rimosus | 10970 | 4% | ND |

ND = Not Determined

EXAMPLE 4

Reduction of Keto Ethyl Ester (VII) to the Corresponding Alcohol (VIII)

Various microbial cultures (1 mL) were inoculated into 100 mL of medium 1 or medium 3 as noted above in a 500 mL flask and incubated at 28° C. and 200 RPM on a shaker for 48 hours. Cells were harvested by centrifugation and cells were suspended in 10 mL of 100 mM potassium phosphate buffer , pH 7.0. Glucose was added to the cell suspensions at 25 mg/mL and 10 mg keto ethyl ester (the substrate see formula VII) was added thereto.

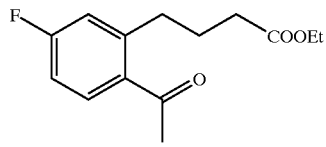

(VII)

The biotransformations (reductions) were carried out at 28° C. and 200 RPM on a shaker. The reaction mixture was extracted with two volumes of ethyl acetate and evaporated to dryness under a stream of nitrogen. A portion of the ethyl acetate extract was dissolved in acetonitrile and analyzed by HPLC method 5 to determine the substrate and product concentrations. Another portion was dissolved in mixture of hexane:isopropanol (1:1) and analyzed by HPLC method 6 to determine the enantiomeric excess of the product. The results are summarized in Table 3 below. The product for this example is as shown in the formula VIII.

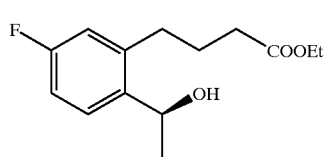

(VIII)

Method 5
Column: Phenylhexyl (0.46×15 cm, 5 micron, Phenomenex)
Mobile Phase: Acetonitrile: Water (1:1)
Flow Rate: 1 ml/min, Detection: UV 210 nm
Retention Times: Keto ethyl ester (VII) 12.4 minutes, Hydroxy ethyl ester (VIII) 8.9 minutes
Method 6
Column: Chiralpak AD (0.46×25 cm, 10 micron, Daicel)
Mobile Phase: Hexane:ethanol:isopropanol (96.9:2.85:0.25)
Flow Rate: 1 ml/min, Detection: UV at 210 nm The enantiomers of (R/S) hydroxy ethyl ester elute at about 15 (R) and 19 (S) minutes.

TABLE 3

Microbial Reduction of Keto Ethyl Ester to the Corresponding (S)-hydroxy Ethyl Ester

| Name | ATCC # | Hydroxy Ethyl Ester | EE of S-Hydroxy Ethyl Ester |
| --- | --- | --- | --- |
| Pichia methanolica | 56508 | 18% | 93.0% |
| Pichia methanolica | 58403 | 51% | >99.9% |
| Geotrichum candidum | 34614 | 33% | 98.5% |

EXAMPLE 5

Reduction of Keto t-butyl Ester (IX) to the Corresponding Alcohol (X)

Various microbial cultures (1 mL) were inoculated into 100 mL of medium 1 or medium 3 as noted above in a 500 mL flask and incubated at 28° C. and 200 RPM on a shaker for 48 hours. Cells were harvested by centrifugation and cells were suspended in 10 mL of 100 mM potassium phosphate buffer , pH 7.0. Glucose was added to the cell suspensions at 25 mg/mL and 10 mg keto t-butyl ester (the substrate see formula IX) was added thereto.

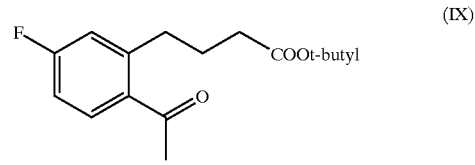

(IX)

The biotransformations (reductions) were carried out at 28° C. and 200 RPM on a shaker. The reaction mixture was extracted with two volumes of ethyl acetate and evaporated to dryness under a stream of nitrogen. A portion of the ethyl acetate extract was dissolved in acetonitrile and analyzed by HPLC method 5 as described in example 4 above to determine the substrate and product concentrations. The retention times are: keto t-butyl ester (IX) 28.3 minutes and hydroxy t-butyl ester (X) 19.2 minutes.

Another portion was dissolved in mixture of hexane:isopropanol (1:1) and analyzed by HPLC method 7 to determine the enantiomeric excess of the product.

Method 7
Column: Chiralpak AD (0.46×25 cm, 10 micron, Daicel)
Mobile Phase: Hexane:isopropanol (90:10)
Flow Rate: 1 ml/min, Detection: UV at 210 nm
The enantiomers of (R/S) hydroxy t-butyl ester elute at about 23.6 (R) and 32.8 (S) minutes.
The results are summarized in Table 4 below. The product for this example is as shown in the Formula (X)

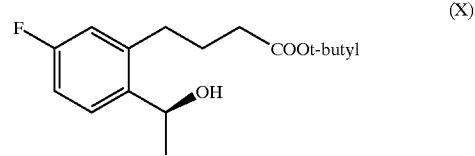

(X)

TABLE 4

Microbial Reduction of Keto t-butyl Ester to the Corresponding (S)-Hydroxy t-butyl Ester

| Name | ATCC # | Hydroxy t-butyl Ester | EE of (S) t-butyl Hydroxy Ester |
|---|---|---|---|
| *Mucor rouxii* | 24905 | 9% | >99% |
| *Mucor hiemalis* | 16636 | 22% | 93% |
| *Pichia methanolica* | 58403 | 4% | 92.6% |

EXAMPLE 6

Reduction of Keto Methyl Ester by Purified Keto-Reductase Enzyme

Purification of Keto-Reductase

A 20% cell suspension of *Pichia methanolica* ATCC 58403 with 10% glycerol, 1 mM DTT, 0.5 mM PMSF, and 10 mM potassium phosphate buffer(pH 7.0) was homogenized prior to cell breakage. The cells were disrupted by passing the cell suspension through a microfluidizer for several passes. The disrupted cell suspension was centrifuged at 18,000 rpm for at least 20 min to remove cell debris. The cell free extract was decanted and used for protein purification. All the purification steps were carried out at 4° C. The purification was carried out using three different conditions for eluting the enzyme from the Hi-Trap Blue-Sepharose affinity column. The protein was loaded on to the affinity column which was equilibrated with buffer A (10% glycerol, 2 mM DTT, and 10 mM potassium phosphate buffer pH 6.5). The protein was eluted from the affinity column by three methods: (1) pH gradient (loading at pH 6.5 and eluting at pH 8.5), (2) NaCl gradient (0 to 0.8 M) in buffer A and (3) NADP gradient (0.1 to 0.5 mM) in buffer A.

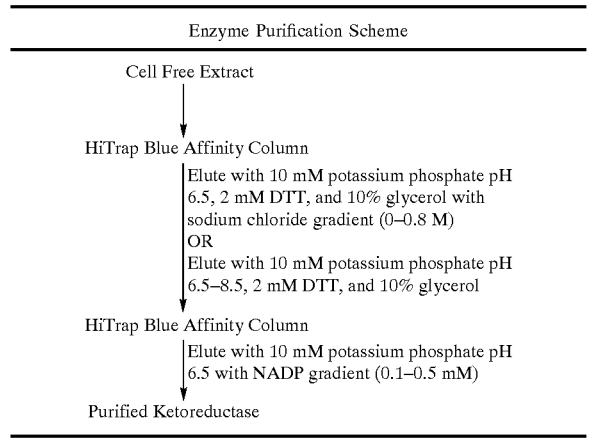

Enzyme Purification Scheme

The enzyme was purified to homogeneity. A molecular weight of ~40 Kd was determined for the purified enzyme. The enzyme is an NADPH-dependent protein. The N-terminal and internal peptide sequences of the protein were determined which will facilitate cloning and overexpression.

```
N-terminal sequence
NH2-x-x-Tyr-Arg-Leu-Val-Arg-Arg-Gln-Arg-Ser-Ala-
Asp-Glu-Gln-COOH
           Internal peptide sequence
Peptide 1:

NH2-Lys-Val-Phe-Phe-Pro-Ala-Pro-Glu-Glu-Tyr-Glu-x-
Phe-Val-Val (Leu)-Phe-Asn-x-x-Phe-Pro-COOH

Peptide 2:

N2-Lys-Val-Pro-Gln-Glu-Leu-Tyr-Thr-Asn-Leu-Gly-
Ser-Ser-Gly-Leu-Gln-Ile-Ser-Lys-COOH

Peptide 3:

N2-Lys-Val-Asp-Asp-Ala-Leu-Asp-Gly-COOH

Note:
x = amino acid not identified.
```

The purified enzyme was tested for the reduction of keto methyl ester (substrate V) to the corresponding (S)-hydroxy methyl ester (product VI). The reaction mixture 5 mL of potassium phosphate buffer (pH 7.0) contained 3 units of purified keto-reductase, 5 mg of substrate V, 0.1 mM NADP, 25 mg of glucose and 15 units of glucose dehydrogenase (to regenerate NADPH). Reaction was carried out as described in the example 3. The substrate V and product VI concentrations and enantiomeric excess of product were determined as described in the example 3. A reaction yield of 90% and an enantiomeric excess of 99.9% were obtained.

EXAMPLE 7

Isolation of the Gene Encoding Ketoreductase from *P. methanolica*

A. Preparation of chromosomal DNA from *P. methanolica*

Stock cultures of *P. methanolica* ATCC 13825 were grown in F7 medium (10.0 g malt extract, 10.0 g yeast extract, 1.0 g peptone, 20.0 g dextrose [pH 7.0] per liter) and stored in vials in 1 ml aliquots under liquid nitrogen. A vial was thawed at room temperature and inoculated into 20 ml YPD medium in a 250 ml flask. YPD consists of, per liter: 10.0 g yeast extract, 20.0 g peptone, and 20.0 g dextrose. The flask was incubated at 30° C. with shaking at 250 rpm for 20 hr. The procedure for rapid isolation of *Saccharomyces cerevisiae* chromosomal DNA was used as written to prepare *P. methanolica* DNA (Ausubel et al., *Current Protocols in Molecular Biology*, John Wiley and Sons, New York, 1990). The precipitated DNA was washed with 70% ethanol, air-dried, and resuspended to a final concentration of 1.0 mg/ml in TE buffer (0.01 $\underline{M}$ Tris-HCl, 0.001 $\underline{M}$ EDTA, pH 8.0) as measured by spectrophotometric analysis at $260_{nm}$.

B. Construction of Partial Sau3A1 Library of *P. methanolica*

*P. methanolica* chromosomal DNA prepared as described in Section 1.A was partially cleaved with restriction endonuclease Sau3A1 in a 0.25 mL reaction volume consisting of 25 μg DNA, 5 units enzyme (Promega, Madison, Wis.), 0.006 $\underline{M}$ Tris-HCl, 0.006 $\underline{M}$ MgCl$_2$, 0.10 $\underline{M}$NaCl, and 0.001 $\underline{M}$ dithiothreitol (pH 7.5) for 5 min at 37° C. The reaction mixture was extracted once with an equal volume of 1:1 phenol:chloroform. After centrifugation, the upper aqueous phase was saved, to which 0.1 vol. of 3 $\underline{M}$ sodium acetate and 0.6 vol. isopropanol was added. DNA was pelleted by centrifugation for 5 min at 16,000×g in a microfuge and washed once with 0.5 mL 70% EtOH. After drying in a SpeedVac (Savant Instruments, Farmingdale, N.Y.) for 5 min, the pellet was resuspended in 0.06 mL TE buffer. The DNA was electrophoresed through a 0.8% agarose gel in TAE buffer (0.04 M Trizma base, 0.02 M acetic acid, and 0.001 M EDTA, pH 8.3) containing 0.5 μg/mL ethidium bromide for 20 hr at 15 v. The region containing DNA fragments of ca. 5–10 kb were identified by comparison to a 1 kb DNA ladder (Life Technologies, Gaithersburg, Md.) and excised from the gel. DNA was extracted using the QIAquick Gel Purification Kit (Qiagen Inc., Valencia, Calif.) following the recommended protocol. An aliquot was electrophoresed on a 0.8% TAE agarose gel for 20 hr at 15 v to confirm the desired fragment size range had been obtained and to determine the concentration of the fragment by comparision to a DNA mass ladder (Life Technologies).

Plasmid pZeroI (Invitrogen, Carlsbad, Calif.) was digested with BamHI (Promega) in a reaction volume of 0.05 μl consisting of 2 μg DNA, 0.006 M Tris-HCl, 0.006 M MgCl$_2$, 0.1 M NaCl, and 0.001 M DTT (pH 7.5). Ten units of restriction endonuclease were added and the mixture incubated at 37° C. for 20 min. The reaction was terminated by addition of an equal volume of 1:1 phenol:chloroform. Following centrifugation at 13,000 ×g for 5 min, the upper (aqueous) phase was removed and placed into a fresh microfuge tube. Five μl of 3M sodium acetate (pH 7.5) and 110 μl of ice-cold 100% ethanol (Shelton Scientific, Shelton, Conn.) were mixed with the aqueous phase and DNA pelleted for 10 min at 13,000 ×g. Any liquid was removed by aspiration and the pellet washed once with 70% ice cold ethanol. The ethanol was removed by aspiration and the pellet dried in a SpeedVac for 5 min. The digested plasmid DNA was resuspended in sterile distilled water to a final concentration of 0.01 mg/ml.

The enriched P. methanolica DNA fragments (5–10 kb) were ligated to BamHI-cleaved pZero2 in a 0.02 mL reaction consisting of 0.1 μg chromosomal DNA, 0.03 μg plasmid DNA, 0.03 M Tris-HCl (pH 7.8), 0.01 M MgCl$_2$, 0.01 M dithiothreitol, and 0.0005 M adenosine-5'-triphosphate and 3 Weiss units of T4 DNA ligase (Promega). The reaction was carried out at 16° C. for 18 hr. DNA was concentrated and salt removed by extraction with 15 μl sterile distilled water and 250 μl 1-butanol. The mixture was centrifuged at 13,000×g for 10 min and all liquid removed by aspiration. The pellet was dried in a SpeedVac for 5 min and resuspended in 5 μl of sterile distilled water. The ligated DNA was transformed into electrocompetent DH10B cells (Life Technologies) according to the vendor's recommendations. Following transformation, 0.96 ml of LB medium was added and the cells grown at 37° C. for 1 hr. A 137 mm Hybond-N+ circle (Amersham-Pharmacia, Piscataway, N.J.) was placed on top of a 150 mm Petri dish containing 75 mL LB agar+kanamycin. An aliquot of the partial Sau3A1 library sufficient to give 5,000 colony forming units was diluted into 1 mL LB medium and spread evenly on the filter. The plate was incubated at 37° C. for 24 hr. Colonies were replicated onto two fresh filters which were placed onto LB +kanamycin agar medium and incubated at 37° C. for 6 hr. Lysis of cells and neutralization of released DNA was performed according to directions that were provided with the filters. The DNA was crosslinked to the filters using a UV Stratalinker 2400 unit (Stratagene, Inc., La Jolla, Calif.) in the "auto crosslink" mode. Cell debris was removed by placing the filters in a container with a solution of 3×SSC (20×SSC contains, per liter, 173.5 g NaCl, 88.2 g sodium citrate, pH adjusted to 7.0 with 10 N NaOH), 0.1% SDS and rubbing the lysed colonies with a wet Kimwipe. The filters were then incubated at least 3 hr with the same wash solution for at least 3 hr at 65° C.

C. Selection of Clones Containing the Ketoreductase Gene

Mixed oligonucleotide primers based on partial amino acid sequences of the purified P. methanolica ketoreductase were prepared (See SEQ ID NO: 7). All possible combinations of sense and anti-sense primers were utilized in polymerase chain reactions (PCR). The reaction consisted of 0.05 M Tris-HCl (pH 8.3), 250 μg/ml bovine serum albumin, 2% (w/v) sucrose, 0.1 mM cresol red, 0.2 mM each dATP, dCTP, dGTP, dTTP, 4 mM MgCl$_2$, 0.0005 mM each primer, 0.25 μl (0.625 U) Takara Z-Taq DNA polymerase (PanVera, Madison, Wis.), and 0.1 μg P. methanolica chromosomal DNA in a total volume of 0.05 ml. Amplification was carried out in a Perkin-Elmer Model 480 Thermal Cycler under the following conditions: Denaturation at 94° C. for 4 min, followed by 30 cycles of 94° C., 1 min; 50° C., 1 min; 72° C., 1.5 min, and a final extension at 72° C. for 5 min. Strong amplification of a 650- and 850-bp fragment respectively was observed using oligonucleotide pairs 183+186 and 185+188 after electorphoresis of a sample of each reactionon a 1.0% TAE agarose gel.

Fragments were isolated from the agaorse gel and purified using the QIAquick Gel Extraction Kit. The DNA was ligated to vector pCR2.1 (Invitrogen, Carlsbad, Calif. ) according to the manufacturer's protocol and transformed into E. coli DH10B by electroporation. Cells were spread onto LB agar medium containing 50 μg/ml kanamycin and Bluo-gal (Life Technologies; 75 μl of a 2% [w/v] solution in dimethylformide) and incubated at 37° C. for 20 hr. Five white colonies chosen at random from each ligation/ transformation were inoculated into LB+kanamycin liquid medium and grown at 37° C., 250 rpm, for 20 hr. Plasmid DNA was prepared from each sample using the QIAprep Spin Miniplasmid Kit (Qiagen). The presence of the expected insert was confirmed by PCR using conditions described above. One representative plasmid was sequenced using the ALFexpress AutoRead kit (Amersham-Phamacia) and analyzed on an ALFexpress automated DNA sequencing unit. In both instances, partial amino acid sequences obtained from the purified enzyme but not used to synthesize oligonucleotides were also found encoded within the PCR fragments. Based on these results, digoxigenin-labeled probes were prepared using the two sets of primers described above and the PCR DIG Probe Synthesis kit (Roche Biochemicals, Indianapolis, Ind.) according to the manufacturer's directions. Ca. 10 ng of the isolated PCR fragment described above was included as template DNA. Amplification conditions were: Denaturation at 94° C. for 4 min, followed by 30 cycles of 94° C., 1 min; 50° C., 1 min, 72° C., 1 min. A 5 μL aliquot of the reaction was electrophoresed on a 1.0% TAE agarose gel along with the non-lableled fragment. Incorporation of the digoxigenin-dUTP nucleotide could be verified by a significant increase in the molecular weight of the labeled fragment. Superior incorporation was obtained using oligonucleotides 183+186.

Duplicate filters containing lysed and denatured DNA from the P. methanolica Sau3A1 library were incubated with 10 ml of DIG EasyHyb solution (Roche) and 5 μL of the denatured, labeled PCR fragment in a roller bottle. Hybridization proceeded at 42° C. for 18 hr. Filters were washed twice with 2×SSC (prepared from a 20×solution; 20×SSC contains, per liter, 173.5 g NaCl, 88.2 g sodium citrate, pH adjusted to 7.0 with 10 N NaOH), 0.1% sodium dodecyl sulfate (SDS) at room temperature for 5 min, then twice at 68° C. with 0.5% SSC, 0.1% SDS for 15 min. Antidigoxigenin antibody binding, washing, and detection were performed using the DIG Labeling and Detection Kit reagents and protocols (Roche). The membranes were placed on Whatman 3MM paper to remove excess liquid, covered with Saran Wrap, and exposed to autoradiography film (Kodak X-OMAT LS). A single hybridizing colony was picked from the master filter and streaked onto LB+kanamycin agar medium and incubated at 37° C. for 24 hr. The colony was grown LB+kanamycin liquid medium for plasmid isolation using the QIAfilter Plasmid Midi Kit (Qiagen). Restriction mapping indicated an insert of ca. 5.0 kb was present in the recombinant plasmid. Isolated DNA was tested for its ability to support amplification using oligos 183+186 and 185+188, which was confirmed. Oligonucleotide primers based on the DNA sequence of the isolated PCR fragments were used for analysis of the insert in pKR5.0. An open reading frame of 1059 bp that encodes a protein of 353 amino acids with a molecular weight of 39,800 daltons was found (SEQ ID NO: 7). This is in near agreement with the size of the isolated ketoreductase (40,000 daltons by gel filtration).

EXAMPLE 8

Subcloning of the *P. methanolica* Ketoreductase Gene and Expression in *Escherichia coli*

The polymerase chain reaction was utilized to amplify the complete ketoreductase gene containing restriction sites suitable for cloning into expression vector pBMS2000. The primers used are given below:

BspHI
a) 5' TGCTCATGAATTGGGAAAAAGTTCCACAAG 3' (nucleotides in bold indicate recognition sequence for restriction enzyme BspHI; underlined nucleotides indicate the initiating Met codon of the ketoreductase gene)

BamHI
b) 5' CTCGGATCCTTATAAAATTACAGAATATAAG 3' (nucleotides in bold indicate recognition sequence for restriction enzyme BamHI; underlined nucleotides indicate the stop codon at the 3' end of the ketoreductase gene)

PCR conditions were identical to those given in section 1.C except pKR5.0 DNA was used as template and the size of the reaction increased to 200 $\mu$l (volumes of all components were increased proportionately). An aliquot of the reaction was electrophoresed on a 1.0% TAE agarose gel to confirm the presence of a band of the expected molecular weight (1077 bp). The remainder of the reaction mix was extracted once with 1:1 phenol:chloroform and the aqueous phase retained after centrifugation at 13,000×g for 5 min. DNA was precipitated by addition of 20 $\mu$l 3 $\underline{M}$ sodium acetate (pH 7.5) and 440 $\mu$l 100% ice-cold ethanol. After centrifugation at 13,000×g for 10 min, liquid was removed by aspiration and the pellet washed with 70% ethanol. The ethanol was aspirated off and the DNA dried in a SpeedVac for 5 min. The pellet was resuspended in 0.043 ml sterile distilled water before digestion in a reaction volume of 0.05 ml consisting of 0.006 $\underline{M}$ Tris-HCl, 0.006 $\underline{M}$ MgCl$_2$, 0.1 M NaCl, and 0.001 $\underline{M}$ DTT (pH 7.5). Ten units (1 $\mu$l) of each restriction endonuclease was added and the mixture incubated at 37° C. for 1.5 hr. The reaction was terminated by addition of an equal volume of 1:1 phenol:chloroform. Following centrifugation at 13,000×g for 5 min, the upper (aqueous) phase was removed and placed into a fresh microfuge tube. Five $\mu$l of 3$\underline{M}$ sodium acetate (pH 7.5) and 110 $\mu$l of ice-cold 100% ethanol (Shelton Scientific, Shelton, Conn.) were mixed with the aqueous phase and DNA pelleted for 10 min at 13,000×g. Any liquid was removed by aspiration and the pellet washed once with 70% ice cold ethanol. The ethanol was removed by aspiration and the pellet dried in a SpeedVac for 5 min. The digested plasmid DNA was resuspended in sterile distilled water to a final concentration of 0.01 mg/ml.

The BspHI/BamHI-digested PCR fragment was ligated to BspHI/BamHI-cleaved pBMS2000 in a 0.02 mL reaction consisting of 0.01 $\mu$g plasmid, 0.03 $\mu$g PCR fragment, 0.03 $\underline{M}$ Tris-HCl (pH 7.8), 0.01 M MgCl$_2$, 0.01 $\underline{M}$ dithiothreitol, and 0.0005 $\underline{M}$ adenosine-5'-triphosphate and 3 Weiss units of T4 DNA ligase (Promega). The reaction was carried out at 16° C. for 18 hr. DNA was concentrated and salt removed by extraction with 15 $\mu$l sterile distilled water and 250 $\mu$l 1-butanol. The mixture was centrifuged at 13,000×g for 10 min and all liquid removed by aspiration. The pellet was dried in a SpeedVac for 5 min and resuspended in 5 $\mu$l of sterile distilled water. The ligated DNA was transformed into electrocompetent DH10B cells (Life Technologies, Inc.) according to the vendor's recommendations. Following transformation, 0.96 ml of LB medium was added and the cells grown at 37° C. for 1 hr. An aliquot of the cells was spread onto LB agar medium containing 10 $\mu$g/ml neomycin sulfate (Sigma) and the plate incubated at 37° C. for 20 hr. The presence of the correct insert was established by PCR using conditions described in section 1.C except a portion of 16 randomly chosen colonies was the source of template DNA. Fourteen out of the 16 colonies amplified a fragment of the correct size. The plasmid from one of these isolates was named pBMS2000-PMKR (for *Pichia methanolica* ketoreductase).

pBMS2000-PMKR was transformed into competent *E. coli* strain BL21-CodonPlus(DE3)-RIL cells (Stratagene) according the manufacturer's protocol. Cells were spread onto LB agar medium containing 30 $\mu$g/ml chloramphenicol and 10 $\mu$g/ml neomycin. Four colonies were randomly chosen and used as a source of template DNA for PCR using the conditions described in section 1.C. All four reactions amplified a DNA fragment of the correct size, demonstrating that that BL21-CodonPlus(DE3)-RIL had been successfully transformed. One of these isolates was selected as the expression strain and used for all further experiments. Vial lots of the expression strain were prepared by culturing the cells at 15° C. in MT3/neo/chlor broth until mid-log phase (OD600~3.5), adding glycerol to 10% final volume, and freezing in liquid nitrogen. The composition of MT3/neo/chlor broth was 1% NZ-Amine A (Sheffield Products, Norwich, N.Y.), 2% Yeastamin (A. E. Staley, Decataur, Ill.), 2% glycerol, 0.6% Na$_2$HPO$_4$, 0.3% KH$_2$PO$_4$, 0.125% (NH$_4$)$_2$ SO$_4$, 0.0246% MgSO$_4$7H$_2$O (EM Science), 10 $\mu$g/ml neomycin sulfate, and 30 $\mu$g/ml chloramphenicol (EM Science).

Expression of the ketoreductase gene was controlled by IPTG (isopropylthio-β-D galactoside) induction of the ptac promoter that originated on plasmid pBMS2000. The expression strain was grown in 25 ml of MT3/neo/chlor in a 250 ml flask at 15° C., 225 RPM until it had reached OD$_{600\ nm}$~0.7. At this point, IPTG (Life Technologies) was added to a final concentration of 0.5 mM. The cultures were allowed to grow overnight (~16 hours) to allow complete induction of the ketoreductase gene and production of the ketoreductase protein.

One ml samples of the overnight expression cultures were transferred to microcentrifuge tubes and the cells were pelleted at 14,000×g for 2 minutes. The supernate was vacuum aspirated and the cell pellet was resuspended in distilled water to attain an OD600 of 30. Ten $\mu$l of the cell suspension was added to 17.5 $\mu$l of distilled water, 10 $\mu$l of 0.5 M dithiothreitol (Sigma) and 12.5 $\mu$l of 4×NuPAGE LDS Protein Sample Loading buffer (Invitrogen). Protein samples were incubated at 70° C. for 10 minutes and 15 $\mu$l aliquots were loaded onto NuPAGE 10% Bis-Tris gels (Invitrogen). Gels were electrophoresed in 1×NuPAGE MOPS SDS Running Buffer at 125 mA until the tracking dye had reached the bottom of the gel. A protein molecular weight standard (Mid-Range Protein Molecular Weight Markers, Promega Corp., Madison, Wis.) was run in an adjacent lane. At the completion of the run the gel was transferred to a tray containing protein staining solution (0.1% Coomassie Blue R250 [Sigma] in 40% ethanol/10% acetic acid/50% water). The solution was placed on a platform shaker and gently agitated for 1 hour. The staining solution was removed and replaced by destaining solution (1×Gel-Clear Destain, Novex). The gel was returned to the platform shaker and destained until the protein bands were clearly visible. The protein sample prepared from the ketoreductase expression strain showed a clearly overexpressed protein with a molecular weight of approximately 40,000 Daltons. Control cultures, either untransformed BL21-CodonPlus(DE3)-RIL or BL21-CodonPlus(DE3)-RIL transformed with pBMS2000, showed no comparable bands following IPTG induction. Subsequent experiments demonstrated that the overexpressed protein was found predominantly in the soluble protein fraction.

In order to test if the heterologously expressed protein possessed ketoreductase activity, the expression strain was grown and induced as described above except that the culture volume was increased to 1 L and the flask size was increased to 4 L. Following overnight induction with IPTG, samples were analyzed on protein gels as described above. The results indicated that scale-up of the culture size had no affect on the strains ability to overexpress the heterologous protein. Example of use of recombinant enzyme in biotransformation process is given in the example 9. Amino acid and nucleotide sequence of ketoeductase protein is given in SEQ ID NO: 7.

SEQUENCE LISTING

```
<160> NUMBER OF SEQ ID NOS: 8

<210> SEQ ID NO 1
<211> LENGTH: 15
<212> TYPE: PRT
<213> ORGANISM: Pichia  methanolica
<220> FEATURE:
<221> NAME/KEY: MISC_FEATURE
<222> LOCATION: (1)..(2)
<223> OTHER INFORMATION: wherein "X" equals any amino acid.

<400> SEQUENCE: 1

Xaa Xaa Tyr Arg Leu Val Arg Arg Gln Arg Ser Ala Asp Glu Gln
1               5                   10                  15

<210> SEQ ID NO 2
<211> LENGTH: 22
<212> TYPE: PRT
<213> ORGANISM: Pichia  methanolica
<220> FEATURE:
<221> NAME/KEY: MISC_FEATURE
<222> LOCATION: (12)..(12)
<223> OTHER INFORMATION: wherein "X" equals any amino acid.
<220> FEATURE:
<221> NAME/KEY: MISC_FEATURE
<222> LOCATION: (19)..(20)
<223> OTHER INFORMATION: wherein "X" equals any amino acid.

<400> SEQUENCE: 2

Lys Val Phe Phe Pro Ala Pro Glu Glu Tyr Glu Xaa Phe Val Val Leu
1               5                   10                  15

Phe Asn Xaa Xaa Phe Pro
            20

<210> SEQ ID NO 3
<211> LENGTH: 19
<212> TYPE: PRT
<213> ORGANISM: Pichia  methanolica

<400> SEQUENCE: 3

Lys Val Pro Gln Glu Leu Tyr Thr Asn Leu Gly Ser Ser Gly Leu Gln
1               5                   10                  15

Ile Ser Lys

<210> SEQ ID NO 4
<211> LENGTH: 8
<212> TYPE: PRT
```

<213> ORGANISM: Pichia methanolica

<400> SEQUENCE: 4

Lys Val Asp Asp Ala Leu Asp Gly
1               5

<210> SEQ ID NO 5
<211> LENGTH: 30
<212> TYPE: DNA
<213> ORGANISM: Pichia methanolica

<400> SEQUENCE: 5
tgctcatgaa ttgggaaaaa gttccacaag                                30

<210> SEQ ID NO 6
<211> LENGTH: 31
<212> TYPE: DNA
<213> ORGANISM: Pichia methanolica

<400> SEQUENCE: 6
ctcggatcct tataaaatta cagaatataa g                              31

<210> SEQ ID NO 7
<211> LENGTH: 1062
<212> TYPE: DNA
<213> ORGANISM: Pichia methanolica
<220> FEATURE:
<221> NAME/KEY: CDS
<222> LOCATION: (1)..(1059)

<400> SEQUENCE: 7

| atg | aat | tgg | gaa | aaa | gtt | cca | caa | gaa | tta | tac | act | cgt | ttg | ggc | tct | 48 |
| Met | Asn | Trp | Glu | Lys | Val | Pro | Gln | Glu | Leu | Tyr | Thr | Arg | Leu | Gly | Ser | |
| 1 | | | | 5 | | | | | 10 | | | | | 15 | | |

| tca | ggt | cta | caa | atc | tcc | aag | att | att | gtt | ggg | tgt | atg | tca | ttc | ggt | 96 |
| Ser | Gly | Leu | Gln | Ile | Ser | Lys | Ile | Ile | Val | Gly | Cys | Met | Ser | Phe | Gly | |
| | | 20 | | | | | 25 | | | | | 30 | | | | |

| acc | aaa | gca | tgg | gga | ggt | gat | tgg | gtt | ttg | gag | gat | gag | gat | gag | atc | 144 |
| Thr | Lys | Ala | Trp | Gly | Gly | Asp | Trp | Val | Leu | Glu | Asp | Glu | Asp | Glu | Ile | |
| | | | 35 | | | | | 40 | | | | | 45 | | | |

| ttt | gcg | att | atg | aaa | aag | gct | tat | gat | caa | ggt | atc | aga | act | ttt | gac | 192 |
| Phe | Ala | Ile | Met | Lys | Lys | Ala | Tyr | Asp | Gln | Gly | Ile | Arg | Thr | Phe | Asp | |
| | 50 | | | | | 55 | | | | | 60 | | | | | |

| act | gct | gac | tct | tat | tct | aat | ggt | gtt | tct | gaa | aga | ctc | tta | ggt | aaa | 240 |
| Thr | Ala | Asp | Ser | Tyr | Ser | Asn | Gly | Val | Ser | Glu | Arg | Leu | Leu | Gly | Lys | |
| 65 | | | | | 70 | | | | | 75 | | | | | 80 | |

| ttc | att | aga | aag | tac | aac | att | gat | aga | tct | aag | ctt | gtt | att | ttg | act | 288 |
| Phe | Ile | Arg | Lys | Tyr | Asn | Ile | Asp | Arg | Ser | Lys | Leu | Val | Ile | Leu | Thr | |
| | | | | 85 | | | | | 90 | | | | | 95 | | |

| aag | gtt | ttt | ttc | cca | gct | cct | gaa | gaa | tat | gag | tcg | ttt | agc | ttc | ttt | 336 |
| Lys | Val | Phe | Phe | Pro | Ala | Pro | Glu | Glu | Tyr | Glu | Ser | Phe | Ser | Phe | Phe | |
| | | | | 100 | | | | | 105 | | | | | 110 | | |

| aat | cat | aat | ttc | cct | ggt | cac | gag | ttg | gtc | aac | aga | agt | ggc | tta | tcg | 384 |
| Asn | His | Asn | Phe | Pro | Gly | His | Glu | Leu | Val | Asn | Arg | Ser | Gly | Leu | Ser | |
| | | | 115 | | | | | 120 | | | | | 125 | | | |

| aga | aaa | cat | att | ttg | gac | tct | gct | gct | gcc | tct | gtt | gag | aga | tta | ggc | 432 |
| Arg | Lys | His | Ile | Leu | Asp | Ser | Ala | Ala | Ala | Ser | Val | Glu | Arg | Leu | Gly | |
| | 130 | | | | | 135 | | | | | 140 | | | | | |

| acc | tat | atc | gat | gta | cta | caa | att | cat | aga | tat | gat | cca | aat | acc | cct | 480 |
| Thr | Tyr | Ile | Asp | Val | Leu | Gln | Ile | His | Arg | Tyr | Asp | Pro | Asn | Thr | Pro | |
| 145 | | | | | 150 | | | | | 155 | | | | | 160 | |

| gct | gaa | gaa | acc | atg | gaa | gct | ttg | aat | gat | tgt | att | aaa | caa | ggt | tta | 528 |

|  |  |
|---|---|
| Ala Glu Glu Thr Met Glu Ala Leu Asn Asp Cys Ile Lys Gln Gly Leu<br>                165                    170                  175 |  |
| acc aga tac att gga gca tct acc atg aga gcc tat caa ttc atc aag<br>Thr Arg Tyr Ile Gly Ala Ser Thr Met Arg Ala Tyr Gln Phe Ile Lys<br>              180                    185                  190 | 576 |
| tat caa aac gtt gct gag aaa cat ggg tgg gca aag ttc atc tcg atg<br>Tyr Gln Asn Val Ala Glu Lys His Gly Trp Ala Lys Phe Ile Ser Met<br>        195                    200                  205 | 624 |
| caa agc tac tac agt tta ctt tac cgt gaa gaa gaa gca gaa cta att<br>Gln Ser Tyr Tyr Ser Leu Leu Tyr Arg Glu Glu Glu Ala Glu Leu Ile<br>    210                    215                  220 | 672 |
| gca tac tgt aat gaa act ggt gtt ggg tta atc cca tgg tca cca aac<br>Ala Tyr Cys Asn Glu Thr Gly Val Gly Leu Ile Pro Trp Ser Pro Asn<br>225                    230                  235                  240 | 720 |
| gct ggt gga ttc tta acc aga cca gta tcc aag caa gac act gcg aga<br>Ala Gly Gly Phe Leu Thr Arg Pro Val Ser Lys Gln Asp Thr Ala Arg<br>              245                    250                  255 | 768 |
| agt gca agt ggg gct gct gcg tta tat ggt cta gaa cct ttc agt gag<br>Ser Ala Ser Gly Ala Ala Ala Leu Tyr Gly Leu Glu Pro Phe Ser Glu<br>        260                    265                  270 | 816 |
| gct gat aag gct att att gac agg gtt gaa gag tta tca aag aaa aag<br>Ala Asp Lys Ala Ile Ile Asp Arg Val Glu Glu Leu Ser Lys Lys Lys<br>    275                    280                  285 | 864 |
| gga gtt tct atg gct agt gtc gct tta gct tgg gtt att agt aag aac<br>Gly Val Ser Met Ala Ser Val Ala Leu Ala Trp Val Ile Ser Lys Asn<br>        290                    295                  300 | 912 |
| agt tgg cca att att ggt ttc agt aag cct gga agg gtt gat gat gct<br>Ser Trp Pro Ile Ile Gly Phe Ser Lys Pro Gly Arg Val Asp Asp Ala<br>305                    310                  315                  320 | 960 |
| tta gat ggt ttc aag ttg aag cta acc gaa gag gac atc aaa ttc tta<br>Leu Asp Gly Phe Lys Leu Lys Leu Thr Glu Glu Asp Ile Lys Phe Leu<br>              325                    330                  335 | 1008 |
| gaa gag cct tat gtt cca aaa cct ttg cct cgc tta tat tct gta att<br>Glu Glu Pro Tyr Val Pro Lys Pro Leu Pro Arg Leu Tyr Ser Val Ile<br>        340                    345                  350 | 1056 |
| tta taa<br>Leu | 1062 |

<210> SEQ ID NO 8
<211> LENGTH: 353
<212> TYPE: PRT
<213> ORGANISM: Pichia methanolica

<400> SEQUENCE: 8

Met Asn Trp Glu Lys Val Pro Gln Glu Leu Tyr Thr Arg Leu Gly Ser
1                 5                    10                   15

Ser Gly Leu Gln Ile Ser Lys Ile Ile Val Gly Cys Met Ser Phe Gly
                20                    25                    30

Thr Lys Ala Trp Gly Gly Asp Trp Val Leu Glu Asp Glu Asp Glu Ile
                35                    40                    45

Phe Ala Ile Met Lys Lys Ala Tyr Asp Gln Gly Ile Arg Thr Phe Asp
        50                    55                    60

Thr Ala Asp Ser Tyr Ser Asn Gly Val Ser Glu Arg Leu Leu Gly Lys
65                    70                    75                    80

Phe Ile Arg Lys Tyr Asn Ile Asp Arg Ser Lys Leu Val Ile Leu Thr
                85                    90                    95

Lys Val Phe Phe Pro Ala Pro Glu Glu Tyr Glu Ser Phe Ser Phe Phe
              100                    105                  110

```
Asn His Asn Phe Pro Gly His Glu Leu Val Asn Arg Ser Gly Leu Ser
        115             120                 125
Arg Lys His Ile Leu Asp Ser Ala Ala Ala Ser Val Glu Arg Leu Gly
        130             135                 140
Thr Tyr Ile Asp Val Leu Gln Ile His Arg Tyr Asp Pro Asn Thr Pro
145             150                 155                 160
Ala Glu Glu Thr Met Glu Ala Leu Asn Asp Cys Ile Lys Gln Gly Leu
                165                 170                 175
Thr Arg Tyr Ile Gly Ala Ser Thr Met Arg Ala Tyr Gln Phe Ile Lys
            180                 185                 190
Tyr Gln Asn Val Ala Glu Lys His Gly Trp Ala Lys Phe Ile Ser Met
        195                 200                 205
Gln Ser Tyr Tyr Ser Leu Leu Tyr Arg Glu Glu Glu Ala Glu Leu Ile
    210                 215                 220
Ala Tyr Cys Asn Glu Thr Gly Val Gly Leu Ile Pro Trp Ser Pro Asn
225             230                 235                 240
Ala Gly Gly Phe Leu Thr Arg Pro Val Ser Lys Gln Asp Thr Ala Arg
                245                 250                 255
Ser Ala Ser Gly Ala Ala Ala Leu Tyr Gly Leu Glu Pro Phe Ser Glu
                260                 265                 270
Ala Asp Lys Ala Ile Ile Asp Arg Val Glu Glu Leu Ser Lys Lys Lys
        275                 280                 285
Gly Val Ser Met Ala Ser Val Ala Leu Ala Trp Val Ile Ser Lys Asn
    290                 295                 300
Ser Trp Pro Ile Ile Gly Phe Ser Lys Pro Gly Arg Val Asp Asp Ala
305                 310                 315                 320
Leu Asp Gly Phe Lys Leu Lys Leu Thr Glu Glu Asp Ile Lys Phe Leu
                325                 330                 335
Glu Glu Pro Tyr Val Pro Lys Pro Leu Pro Arg Leu Tyr Ser Val Ile
            340                 345                 350
Leu
```

EXAMPLE 9

Reduction of Keto Methyl Ester (V) by Recombinant *Escherichia coli* Expressing Keto-reductase from *Pichia methanolica*

Keto-reductase gene from *Pichia methanolica* was cloned and overexpressed in *Escherichia coli*. Cells of *Escherichia coli* (expressing keto-reductase) were grown in a 15-L and 250-L fermentor in medium 5. Induction of Keto-reductase in *Escherichia coli* was carried out at optical cell density (OD) of culture was reached to 3.0 by the addition of 0.25 mM isopropyl-β-thiogalactoside (IPTG) as an inducer. Cells were harvested after 30 hours growth in a fermentor after addition of IPTG. Cells were used to catalyze the bioconversion of keto methyl ester (substrate V) to the corresponding (S)-hydroxy methyl ester (product VI) by cell suspensions.

The substrate and the product for this Example were as described in Example 3. Cells of *Escherichia coli* expressing Ketoreductase enzyme were suspended in 1-L of 100 mM phosphate buffer pH 7.0 suspensions were supplemented with 100 μM nicotinamide adenine dinucleotide phosphate (NADP), 1 mM phenylmethane sulfonyl fluoride (PMSF), 50 grams glucose, 3400 units glucose dehydrogenase, and 4.5 grams substrate (keto methyl ester, Formula V). Biotransformation was carried out at 500 RPM and at 28° C. temperature. Substrate V and product VI concentrations and enantiomeric excess of product VI were determined by HPLC analysis as described in the example 3. The reaction was completed in 20 hours with a reaction yield of product (hydroxymethyl ester, Formula VI) of 95%. The enantiomeric excess of 99.9% was obtained for product VI.

What is claimed is:

1. A process for the preparation of a compound of Formula (I)

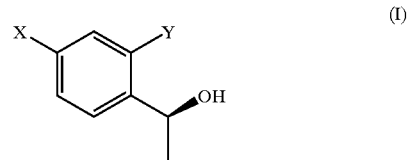

Wherein
X is F, Cl, I or $R^1$;
Cl, Br, I or $R^1$;
$R^1$ is substituted or unsubstituted alkyl, alkenyl or $(CH_2)_nCOR^2$;

n is an integer from 1 to 10;
R² is OH, OR³ or NH₂; and
R³ is substituted or unsubstituted alkyl, alkenyl, C₃₋₇cycloalkyl or substituted or unsubstituted aryl;
by stereoselective reduction of a compound of Formula (II)

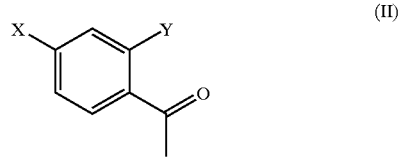
(II)

wherein
X Is F, Cl, Br or I; and
Cl, Br, I or R¹;
R¹ is substituted or unsubstituted alkyl, alkenyl, or $(CH_2)_nCOR^2$;
n is an integer from 1 to 10;
R² is OH, OR³ or NH₂; and
R⁹ is substituted or unsubstituted alkyl, alkenyl, C₃₋₇cycloalkyl or substituted or unsubstituted aryl;
by reaction with an oxidoreductase enzyme capable of catalyzing the enzymatic reduction of ketones represented by Formula (II), wherein said oxidoreductase enzyme is the *Pichia methanoilca* ketoreductase of SEQ ID NO. 7 as expressed in *Eschericha Coli*.

2. The process of claim 1 where X is F and Y is Br.

3. The process of claim 1 where X is F and Y is R¹ which is $(CH_2)_nCOOR^3$ where R₃ is alkyl.

4. A process for the preparation of a compound of Formula (I)

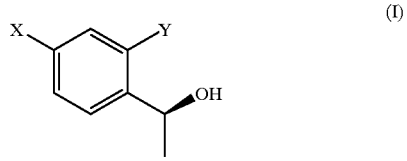
(I)

wherein
X is F, Cl, Br, I or R¹; and
Cl, Br, I or R¹;
R¹ is substituted or unsubstituted alkyl, alkenyl, or $(CH_2)_nCOR^2$,
n is an integer from 1 to 10;
R² is OH, OR³ or NH₂; and
R³ is substituted or unsubstituted alkyl, alkenyl, C₃₋₇cycloalkyl or substituted or unsubstituted aryl;
by stereoselective reduction of a compound of Formula (II)

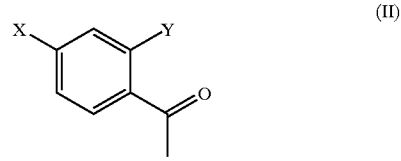
(II)

wherein
X is F, Cl, Br, I or R¹; and
Cl, Br, I, or R¹;
R¹ is substituted or unsubstituted alkyl, alkenyl or $(CH_2)_nCOR^2$;
n is an integer from 1 to 10;
R² is OH, OR³ or NH₂; and
R³ is substituted or unsubstituted alkyl, alkenyl, C₃₋₇ cyoloalkyl or substituted or unsubstituted aryl;
comprising reacting said compound of Formula (II) with a microorganism that supplies an oxidoreductase enzyme capable of catalyzing the enzymatic reduction of ketones represented by Formula (II), wherein the microorganism Is *Candida sonorensis, Candida boidini, Candida guilliermondi, Candida utilis, Candida maltosa, Candida kefir, Candida parapslosis, Geotrichum candidum, Rhodotorula glutinis, Hansenula fabianii, Hansenula polymorpha, Hansenula saturnus, Nocardia salmonicolor, Pichia anomala, Pichia capsulata, Pichia membranafaciens, Pichia methanolica, Pichia pinus, Pichia silvicola, Pichia stipitis, Sphingomonas paucimobilis, Saccharomyces cerevisiae, Yeast*, and *Baker's Yeast*.

5. The process of claim 4 wherein said microorganism that supplies an oxidoreductase enzyme is selected from the group consisting of *Pichia methanolica* ATCC 56510, *Pichia methanolica* ATCC 56508 and *Pichia methanolica* ATCC 58403 and wherein said oxidoreductase is ketoreductase.

6. The process of claim 4 wherein the microorganism is *Saccharomyces cerevisiae*.

7. The process of claim 4 where X is F and Y is Br.

8. The process of claim 4 where X is F and Y is R¹ which is $(CH_2)_nCOOR^3$ where R³ is alkyl.

9. The process of claim 4 wherein X is F and Y is Br.

* * * * *

UNITED STATES PATENT AND TRADEMARK OFFICE
CERTIFICATE OF CORRECTION

PATENT NO. : 6,800,477 B2 Page 1 of 1
DATED : October 5, 2004
INVENTOR(S) : Patel et al.

It is certified that error appears in the above-identified patent and that said Letters Patent is hereby corrected as shown below:

Column 27,
Line 18, "Cl, Br, I or $R^1$;" should read -- Y is Cl, Br, I or $R^1$; --

Column 28,
Line 16, "Cl, Br, I or $R^1$;" should read -- Y is Cl, Br, I or $R^1$; --
Line 45, "The process of claim 4 where X is F and Y is Br." should read -- The process of claim 1 where X is F and Y is Br. --

Signed and Sealed this

First Day of March, 2005

JON W. DUDAS
*Director of the United States Patent and Trademark Office*